US012673904B2

(12) United States Patent
Dong et al.

(10) Patent No.: US 12,673,904 B2
(45) Date of Patent: Jul. 7, 2026

(54) MICROBIAL INOCULANT FOR HIGH-SPEED HUMIFICATION OF ORGANIC WASTE AND PREPARATION METHOD THEREOF

(71) Applicant: Tongji University, Shanghai (CN)

(72) Inventors: Bin Dong, Shanghai (CN); Xinru Zhong, Shanghai (CN); Xin Li, Shanghai (CN); Haoxuan Han, Shanghai (CN); Danni Shen, Shanghai (CN); Zuxin Xu, Shanghai (CN)

(73) Assignee: Tongji University, Shanghai (CN)

( * ) Notice: Subject to any disclaimer, the term of this patent is extended or adjusted under 35 U.S.C. 154(b) by 609 days.

(21) Appl. No.: 18/140,638

(22) Filed: Apr. 28, 2023

(65) Prior Publication Data

US 2023/0416167 A1    Dec. 28, 2023

(30) Foreign Application Priority Data

Jun. 24, 2022    (CN) .......................... 202210728902.1

(51) Int. Cl.
| | |
|---|---|
| *C05F 11/08* | (2006.01) |
| *C12N 1/205* | (2026.01) |
| *C12R 1/01* | (2006.01) |
| *C12R 1/07* | (2006.01) |

(52) U.S. Cl.
CPC .............. *C05F 11/08* (2013.01); *C12N 1/205* (2021.05); *C12N 2500/12* (2013.01); *C12N 2500/32* (2013.01); *C12N 2500/34* (2013.01);

*C12N 2500/84* (2013.01); *C12R 2001/01* (2021.05); *C12R 2001/07* (2021.05)

(58) Field of Classification Search
CPC .......... C05F 11/08; C05F 17/20; C12N 1/205; C12N 2500/12; C12N 2500/32; C12N 2500/34; C12N 2500/84; C12N 1/20; C12N 11/14; C12R 2001/01; C12R 2001/07; Y02W 30/40; B09B 3/60
See application file for complete search history.

*Primary Examiner* — Kade Ariani
(74) *Attorney, Agent, or Firm* — OPENPTO US LLC; Yuhao Liang

(57) ABSTRACT

A microbial inoculant for high-speed humification of organic waste and a preparation method thereof are provided. According to the present disclosure, the microbial inoculant is prepared from *Geobacillus stearothermophilus* GT1, *Thermus tengchongensis* GT2, and *Thermus amyloliquefaciens* GT3. According to the present disclosure, the microbial inoculant prepared from hyperthermophiles with different functions directionally degrades proteins, promotes humification, and degrades complex polysaccharides and organic waste. The resulting products contain rich surface oxygen-containing functional groups, which can adsorb heavy metals and reduce the heavy metal migration rate. Meanwhile, the preparation method of the microbial inoculant provided by the present disclosure can solve the problem that multiple microbial strains are difficult to enrich, and materials for preparing the microbial inoculant can be recycled, which are environmentally friendly and free of secondary pollution.

7 Claims, No Drawings

MICROBIAL INOCULANT FOR HIGH-SPEED HUMIFICATION OF ORGANIC WASTE AND PREPARATION METHOD THEREOF

CROSS REFERENCE TO THE RELATED APPLICATIONS

This application is based upon and claims priority to Chinese Patent Application No. 202210728902.1, filed on Jun. 24, 2022, the entire contents of which are incorporated herein by reference.

TECHNICAL FIELD

The present disclosure belongs to the technical field of organic waste degradation, and relates to a microbial inoculant for high-speed humification of organic waste and a preparation method thereof.

BACKGROUND

The discovery of hyperthermophiles provides the possibility for the realization of ultra-high-temperature aerobic composting. Since Japanese scientists used hyperthermophiles in ultra-high-temperature aerobic fermentation of sludge, ultra-high-temperature aerobic fermentation has gradually become a hot topic. However, how to develop and utilize hyperthermophiles on a large scale seems to be a challenge for the promotion of ultra-high-temperature aerobic fermentation. The genus *Geobacillus* is a representative genus of hyperthermophiles. The vegetative cells of *Geobacillus stearothermophilus* present a round-ended long rod shape, most of which are single and a few of which are arranged in pairs or chains. The formation time of the colonies is generally more than 24 h.

The thermophilic enzyme contained in the genus *Thermus* has a high-temperature resistant property, which makes it widely used in special industries, including the organic waste disposal industry. The organic waste with starch and wood cellulose as raw materials can be disposed of well in the presence of the thermophilic enzyme. However, *Thermus* colonies are too small to collect easily. At the same time, it is found that hyperthermophiles are very easy to form biofilms and produce thermophilic spores. This feature enables the genus *Thermus* to adhere to inorganic surfaces through electrostatic interaction, and spores are easier to adhere to than vegetative bodies. If a technology can be used to enrich and grow hyperthermophiles on the surface of inorganic cores, this problem can be tried to break through.

Ultra-high-temperature aerobic fermentation technology can effectively increase the fermentation temperature, enhance the humification degree of materials, effectively kill pathogenic microorganisms, and shorten the fermentation cycle. However, it also has obvious defects. For example, hyperthermophiles compete with indigenous microorganisms (common aerobic microorganisms) at a disadvantage, and if different bacterial genera are cultured at the same time, antagonism may occur, so that bacterial strains cannot be enriched and grown. Using a single hyperthermophilic microbial inoculant may not be effective in treating different types of organic waste, and cannot achieve the directional promotion of humification on materials. Therefore, if hyperthermophiles for degrading different organic matters (rich in proteins, polysaccharides, etc.) can be used and compounded into microbial inoculants without mutual influence, the organic waste can be disposed of more efficiently and thoroughly.

SUMMARY

To solve the problems in the prior art, the present disclosure provides a microbial inoculant for high-speed humification of organic waste and a preparation method thereof. The present disclosure adopts albite beads which do not biochemically react with hyperthermophiles, and compound hyperthermophiles are cultured together with the beads so that the hyperthermophiles can be enriched on the surface of the beads to prepare the microbial inoculant for use. The microbial inoculant provided by the present disclosure can not only deeply decompose the organic waste, but also promote the directional decomposition of the organic waste to produce more functional groups of humic substances (carboxyl, phenolic hydroxyl, etc.) that are beneficial to the immobilization of heavy metals.

To achieve the above objective, the present disclosure adopts the following technical solutions.

In the first aspect, the present disclosure provides a preparation method of a microbial inoculant for high-speed humification of organic waste, including the following steps:

step 1, initial culture: preparing a culture medium, and adding albite beads, *Thermus tengchongensis* GT2, and *Thermus amyloliquefaciens* GT3 to the culture medium; culturing at 55-85° C. for 24-128 h, energizing the culture medium at a weak current of 5-15 mA, and connecting a negative electrode, to make bacterial strains gather to the beads;

step 2, membrane-covered enrichment culture: continuing to add 10-50 mg/L $Fe^{3+}$ and *Geobacillus stearothermophilus* GT1 to the culture medium, and culturing at 65-75° C. for 5-72 h;

step 3, membrane removal: taking out the albite beads, putting the albite beads into an electrolysis unit, and treating for 0.5-2 h at a current of 16-25 A to obtain a biofilm; and step 4, preparation of the microbial inoculant: adding 5-15% (m/v) of activated carbon particles, and drying or freeze-drying to obtain the microbial inoculant.

Further, the GT1 is a *G. stearothermophilus* strain deposited at the China General Microbiological Culture Collection Center (CGMCC) on Jul. 19, 2021, with an accession number of CGMCC No. 22925.

Further, the GT2 is a *T. tengchongensis* strain deposited at the CGMCC on Jul. 19, 2021, with an accession number of CGMCC No. 22927.

Further, the GT3 is a *T. amyloliquefaciens* strain deposited at the CGMCC on Jul. 19, 2021, with an accession number of CGMCC No. 22928.

Further, the culture medium is formulated with 8-12 g/L tryptone, 5-7 g/L casein, 3-5 g/L glucose, 3-5 g/L sodium chloride, 2-4 g/L disodium hydrogen phosphate, 10-14 g/L dehydrated calf brain infusion, and 8-12 g/L agar and has a pH ranging from 6.8 to 7.2.

Further, the dosage of the albite beads is 5-15% (m/v) of that of a bacterial culture medium, the albite beads are 5-12 mm in diameter, and the activated carbon particles are 0.5-1.5 mm in diameter.

Further, on condition that proteins in the organic waste account for ≥60% of organic matter, a ratio of volume percentages of the strains (GT1:GT2:GT3) is (3-5):(0.8-1.2):(0.6-1.4).

Further, on condition that complex polysaccharides in the organic waste account for ≥60% of organic matter, a ratio of volume percentages of the strains (GT1:GT2:GT3) is (0.4-0.9):(8-10):(0.5-1.2).

Further, on condition that simple polysaccharides in the organic waste account for ≥60% of organic matter, a ratio of volume percentages of the strains (GT1:GT2:GT3) is (0.6-0.8):(0.7-1.3):(6-15).

In a second aspect, the present disclosure further provides a microbial inoculant prepared by the foregoing preparation method and use thereof in organic waste disposal.

Compared with the prior art, the present disclosure has the following advantages:

1. Most of *Geobacillus* species are single, a few ones are arranged in pairs or chains, and the colony formation time generally takes more than 24 h. *Thermus* colonies are too small to collect easily. Hyperthermophiles are extremely easy to form biofilms and produce thermophilic spores. This feature enables the *Thermus* species, GT2 and GT3, to adhere to inorganic surfaces through electrostatic interaction, so that hyperthermophiles that are difficult to aggregate are enriched into biofilms to solve technical problems of difficulty in the collection.

2. Using differences in EPS viscosity and components of *Thermus* species (GT2 and GT3) and *Geobacillus* species (GT1), thick biofilms are formed by culture in stages. It not only avoids the mutual influence of different bacterial species, but also forms and thickens the biofilm.

3. According to the present disclosure, hyperthermophiles with different functions (use of GT1 in protein degradation and directional promotion of humification, use of GT2 in degrading complex polysaccharides (such as cellulose and lignin), and use of GT3 in degrading simple polysaccharides (such as starch and sucrose)) are compounded to prepare a microbial inoculant, which can dispose of different types of organic waste. The resulting products contain rich surface oxygen-containing functional groups, which can absorb heavy metals and reduce the heavy metal migration rate.

4. In the present disclosure, biochar particles are added in the freeze-drying process to increase the particle size of the microbial inoculant, with high feasibility and easy operation.

Deposit of Biological Material

GT1: *G. stearothermophilus* strain deposited at the CGMCC on Jul. 19, 2021, with an accession number of CGMCC No. 22925.

GT2: a *T. tengchongensis* strain deposited at the CGMCC on Jul. 19, 2021, with an accession number of CGMCC No. 22927.

GT3: a *T. amyloliquefaciens* strain deposited at the CGMCC on Jul. 19, 2021, with an accession number of CGMCC No. 22928.

DETAILED DESCRIPTION OF THE EMBODIMENTS

The present disclosure will be described in detail below with reference to specific examples. The following examples will help those skilled in the art further understand the present disclosure, but do not limit the present disclosure in any way. It should be noted that those of ordinary skill in the art can further make several variations and improvements without departing from the spirit of the present disclosure. All of these fall within the protection scope of the present disclosure.

A culture medium used in the following examples is formulated with 10 g/L tryptone, 6 g/L casein, 4 g/L glucose, 4 g/L sodium chloride, 3 g/L disodium hydrogen phosphate, 12 g/L, dehydrated calf brain infusion, and 10 g/L agar and has a pH ranging from 6.8 to 7.2.

EXAMPLE

A preparation method of a microbial inoculant for high-speed humification of organic waste specifically included the following steps:

step 1, initial culture: a culture medium was prepared, and albite beads, bacterial stains GT2 and GT3 were added to the culture medium; the culture system was cultured at 80° C. for 96 h, and the culture medium was energized at a weak current of 10 mA, and a negative electrode was connected to make bacterial strains gather to the beads;

step 2, membrane-covered enrichment culture: 25 mg/L $Fe^{3+}$ and strain GT1 were further added to the culture medium, and cultured at 72° C. for 36 h; the ratio of volume percentages of strains (GT1:GT2:GT3) was 4:1.2:1.3;

step 3, membrane removal: the albite beads were taken out, put into an electrolysis unit, and treated for 1.2 h at a current of 16 A to obtain a biofilm; and step 4, preparation of the microbial inoculant: 15% of activated carbon particles were added, and dried or freeze-dried to obtain the microbial inoculant.

After the well-prepared microbial inoculant was mixed evenly with protein-rich organic waste (protein/organic matter ≥60%) at a weight ratio of 1:5, the initial moisture content was 55%. The fermentation time was 15 days, and the highest fermentation temperature was higher than 85° C. (which was maintained for more than 5 days). The waste disposal was carried out under the above conditions, and its humus content (characterized by humic carbon content) could reach 120-250 mg/g VS, When the humus content of the waste before fermentation reached 120-250 mg/g VS, the humus content of the fermented sludge could increase by 2-5 times, where the content of soluble humus was 25-60 mg/g VS. When the content of soluble humus before fermentation reached 25-60 mg/g VS, the content of soluble humus after fermentation could increase by 6-15 times.

Example 2

A preparation method of a microbial inoculant for high-speed humification of organic waste specifically included the following steps:

step 1, initial culture: a culture medium was prepared, and albite beads, bacterial stains GT2 and GT3 were added to the culture medium; the culture system was cultured at 75° C. for 112 h, and the culture medium was energized at a weak current of 5 mA, and a negative electrode was connected to make bacterial strains gather to the beads;

step 2, membrane-covered enrichment culture: 15 mg/L $Fe^{3+}$ and strain GT1 were further added to the culture medium, and cultured at 65° C. for 48 h; the ratio of volume percentages of strains (GT1:GT2:GT3) was 0.7:8:1.1;

step 3, membrane removal: the albite beads were taken out, put into an electrolysis unit, and treated for 0.5 h at a current of 20 A to obtain a biofilm; and step 4, preparation of the microbial inoculant: 12% of activated carbon particles were added, and dried or freeze-dried to obtain the microbial inoculant.

After the well-prepared microbial inoculant was mixed evenly with complex polysaccharides-rich organic waste (complex polysaccharides/organic matter ≥60%) at a weight ratio of 1:5, the initial moisture content was 50%. The fermentation time was 21 days, and the highest fermentation temperature was higher than 85° C. (which was maintained for more than 3 days). The waste disposal was carried out under the above conditions, and its humus content (characterized by humic carbon content) could reach 80-200 mg/g VS. When the humus content of the waste before fermentation reached 80-200 mg/g VS, the humus content of the fermented sludge could increase by 2-4 times, where the content of soluble humus was 15-45 mg/g VS. When the content of soluble humus before fermentation reached 15-45 mg/g VS, the content of soluble humus after fermentation could increase by 5-15 times.

Example 3

A preparation method of a microbial inoculant for high-speed humification of organic waste specifically included the following steps:

step 1, initial culture: a culture medium was prepared, and albite beads, bacterial stains GT2 and GT3 were added to the culture medium; the culture system was cultured at 85° C. for 128 h, the culture medium was energized at a weak current of 12 mA, and a negative electrode was connected to make bacterial strains gather to the beads;

step 2, membrane-covered enrichment culture: 20 mg/L $Fe^{3+}$ and strain GT1 were further added to the culture medium, and cultured at 65-75° C. for 5-72 h; the ratio of volume percentages of strains (GT1:GT2:GT3) was 0.8:0.7:15;

step 3, membrane removal: the albite beads were taken out, put into an electrolysis unit, and treated for 1 h at a current of 18 A to obtain a biofilm; and step 4, preparation of the microbial inoculant: 10% of activated carbon particles were added, and dried or freeze-dried to obtain the microbial inoculant.

After the well-prepared microbial inoculant was mixed evenly with simple polysaccharides-rich organic waste (simple polysaccharides/organic matter ≥60%) at a weight ratio of 1:5, the initial moisture content was 53%. The fermentation time was 18 days, and the highest fermentation temperature was higher than 85° C. (which was maintained for more than 5 days). The waste disposal was carried out under the above conditions, and its humus content (characterized by humic carbon content) could reach 100-200 mg/g VS. When the humus content of the waste before fermentation reached 100-200 mg/g VS, the humus content of the fermented sludge could increase by 2-6 times, where the content of soluble humus was 25-70 mg/g VS. When the content of soluble humus before fermentation reached 25-70 mg/g VS, the content of soluble humus after fermentation could increase by 6-12 times.

What is claimed is:

1. A preparation method of a microbial inoculant for a high-speed humification of an organic waste, comprising the following steps:

step 1, initial culturing by preparing a culture medium, and adding albite beads, *Thermus tengchongensis* GT2, and *Thermus amyloliquefaciens* GT3 to the culture medium;

culturing at 55-85° C. for 24-128 h, energizing the culture medium at a weak current of 5-15 mA, and connecting a negative electrode, to make the *Thermus tengchongensis* GT2 and the *Thermus amyloliquefaciens* GT3 gather to the albite beads;

step 2, membrane-covered enrichment culturing by adding 10-50 mg/L Fe3+ and *Geobacillus stearothermophilus*GT1 to the culture medium, and culturing at 65-75° C. for 5-72 h;

step 3, membrane removing by taking out the albite beads, putting the albite beads into an electrolysis unit, and treating for 0.5-2 h at a current of 16-25 A to obtain a biofilm; and step 4, preparing the microbial inoculant by adding 5-15% of activated carbon particles to the biofilm, and drying or freeze-drying to obtain the microbial inoculant;

wherein proteins, complex polysaccharides, or simple polysaccharides in the organic waste account for ≥60% of organic matter, the complex polysaccharides are selected from the group consisting of cellulose and lignin, and the simple polysaccharides are selected from the group consisting of starch and sucrose; and the *Geobacillus stearothermophilus*GT1 is a *Geobacillus stearothermophilus* strain deposited at the China General Microbiological Culture Collection Center (CGMCC) on Jul. 19, 2021, with an accession number of CGMCC No. 22925; the *Thermus tengchongensis* GT2 is a *Thermus tengchongensis* strain deposited at the CGMCC on Jul. 19, 2021, with an accession number of CGMCC No. 22927; and the *Thermus amyloliquefaciens* GT3 is a *Thermus amyloliquefaciens* strain deposited at the CGMCC on Jul. 19, 2021, with an accession number of CGMCC No. 22928.

2. The preparation method according to claim 1, wherein the culture medium is formulated with 8-12 g/L tryptone, 5-7 g/L casein, 3-5 g/L glucose, 3-5 g/L sodium chloride, 2-4 g/L disodium hydrogen phosphate, 10-14 g/L dehydrated calf brain infusion, and 8-12 g/L agar and the culture medium has a pH ranging from 6.8 to 7.2.

3. The preparation method according to claim 1, wherein a dosage of the albite beads is 5-15% of the culture medium, each of the albite beads is 5-12 mm in diameter, and each of the activated carbon particles is 0.5-1.5 mm in diameter.

4. A microbial inoculant prepared by the preparation method according to claim 1.

5. A method of disposing of the organic waste, comprising mixing the microbial inoculant according to claim 4 with the organic waste, wherein the proteins, the complex polysaccharides, or the simple polysaccharides in the organic waste account for ≥60% of the organic matter, the complex polysaccharides are selected from the group consisting of the cellulose and the lignin, and the simple polysaccharides are selected from the group consisting of the starch and the sucrose.

6. The microbial inoculant according to claim 4, wherein the culture medium is formulated with 8-12 g/L tryptone, 5-7 g/L casein, 3-5 g/L glucose, 3-5 g/L sodium chloride, 2-4 g/L disodium hydrogen phosphate, 10-14 g/L dehydrated calf brain infusion, and 8-12 g/L agar and the culture medium has a pH ranging from 6.8 to 7.2.

7. The microbial inoculant according to claim 4, wherein a dosage of the albite beads is 5-15% of the culture medium, each of the albite beads is 5-12 mm in diameter, and each of the activated carbon particles is 0.5-1.5 mm in diameter.

* * * * *